United States Patent
Bostick et al.

(10) Patent No.: US 10,195,611 B2
(45) Date of Patent: Feb. 5, 2019

(54) METHOD AND APPARATUS FOR ORIENTING PIPETTE TIPS

(71) Applicant: PRODUCTIVE LABS, LLC, Morgantown, WV (US)

(72) Inventors: Chris Bostick, Windsor, NJ (US); Emily Despeaux, Morgantown, WV (US); Tyler Davis, Charlotte, NC (US); Alice Han, Clarksburg, MD (US); William Mandler, Morgantown, WV (US); Kelly Pisane, Coralville, IA (US)

(*) Notice: Subject to any disclaimer, the term of this patent is extended or adjusted under 35 U.S.C. 154(b) by 222 days.

(21) Appl. No.: 15/380,041

(22) Filed: Dec. 15, 2016

(65) Prior Publication Data

US 2017/0165673 A1 Jun. 15, 2017

Related U.S. Application Data

(60) Provisional application No. 62/267,638, filed on Dec. 15, 2015.

(51) Int. Cl.
*B01L 9/00* (2006.01)
*G01N 35/10* (2006.01)

(52) U.S. Cl.
CPC ......... *B01L 9/543* (2013.01); *B01L 2200/025* (2013.01); *G01N 2035/103* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,100,021 A | * | 3/1992 | Mussi | B01L 9/543 221/155 |
| 5,568,881 A | * | 10/1996 | Chi | B01L 9/543 221/172 |
| 6,368,872 B1 | * | 4/2002 | Juranas | G01N 35/10 414/416.01 |
| 6,599,476 B1 | * | 7/2003 | Watson | B65G 47/1471 141/1 |
| 2003/0047418 A1 | * | 3/2003 | Okada | B65G 47/1471 198/459.1 |
| 2004/0031809 A1 | * | 2/2004 | Itoh | B01L 9/543 221/208 |
| 2004/0108330 A1 | * | 6/2004 | Itoh | B01L 9/543 221/289 |
| 2007/0148042 A1 | * | 6/2007 | Ootani | G01N 35/10 422/63 |
| 2007/0231215 A1 | * | 10/2007 | Mototsu | B01L 3/0275 422/400 |
| 2008/0138184 A1 | * | 6/2008 | Carmi | B01L 9/543 414/745.7 |

(Continued)

*Primary Examiner* — Brian R Gordon
(74) *Attorney, Agent, or Firm* — Birch, Stewart, Kolasch & Birch, LLP

(57) ABSTRACT

A pipette tip orienting apparatus includes a hopper adapted for receiving one or more pipette tips. A first alignment comb is inserted thorugh the hopper for orienting pipette tips inside the hopper. A second alignment comb is inserted through the hopper for orienting the pipette tips for delivery to a pipette tip rack. The first and second alignment combs are positioned perpendicular to one another through the hopper. Pipette tips are delivered to wells in a pipette tip rack by removing the alignment combs sequentially from the hopper.

19 Claims, 2 Drawing Sheets

(56) References Cited

U.S. PATENT DOCUMENTS

| | | | | |
|---|---|---|---|---|
| 2009/0078717 A1* | 3/2009 | Kowari | ............... | G01N 35/04 |
| | | | | 221/1 |
| 2009/0081081 A1* | 3/2009 | Kowari | ............... | B01L 9/543 |
| | | | | 422/63 |
| 2010/0294620 A1* | 11/2010 | Chi | ............... | B65B 5/101 |
| | | | | 198/397.01 |
| 2012/0195798 A1* | 8/2012 | Kowari | ............... | G01N 35/04 |
| | | | | 422/69 |
| 2014/0076920 A1* | 3/2014 | Tsukioka | ............... | B01L 9/543 |
| | | | | 221/248 |
| 2015/0044111 A1* | 2/2015 | Peetz | ............... | B01L 9/543 |
| | | | | 422/511 |

* cited by examiner

METHOD AND APPARATUS FOR ORIENTING PIPETTE TIPS

FIELD OF INVENTION

This application relates generally to an apparatus for organizing and dispensing scientific tools, and, more particularly, it relates to sorting and organizing pipette tips.

BACKGROUND

A significant number of pipette tips are used daily in a clinical laboratory. Each pipette tip is used once and then discarded to avoid contamination. Pipette tips generally are positioned for use on the laboratory bench top in racks. Pipette tip racks have rows and columns of wells, each well adapted for receiving a pipette tip. Pipette tips are tapered along their length, and the tips must be placed in the rack wells narrow tip end first.

Refilling pipette tip racks with pipette tips by hand can be a burdensome and time-consuming task. To expedite the process and to ease the burden on laboratory staff, products are offered in which pipette tips come pre-configured in rows and columns corresponding to the rows and columns in the pipette tip rack being used. To refill the rack, an entire lot of pipette tips can be lowered into the wells simultaneously. While more convenient for the laboratory staff, these pre-configured and packaged pipette tips are significantly more expensive than unconfigured pipette tips purchased in bulk, at least in part due to the packaging cost and materials.

The alternative to preconfigured pipette tips is to purchase the pipette tips in bulk at a lower price. The bulk pipette tips often come in large plastic bags that contain hundreds or thousands of pipette tips. While purchasing pipette tips in bulk provides an up-front savings, the result is an increased workload for the laboratory staff because the pipette tips must be loaded into the pipette tip rack manually one at a time. It is not uncommon for laboratory personnel to expend an hour a day refilling pipette tip racks. Thus, there is a need in the industry for an efficient means for loading pipette tips that have been purchased in bulk and that are delivered in large quantity bags into pipette tip racks.

SUMMARY

The present invention solves the foregoing problems by providing a hopper adapted for receiving a plurality of bulk pipette tips with no regard for pipette tip orientation, and first and second alignment combs for orienting and positioning the pipette tips to correspond to the wells in a pipette tip rack.

A first aspect of the invention is an apparatus including a (i) hopper adapted for receiving one or more pipette tips, the hopper having a top opening and a bottom opening, wherein the top opening is larger than the bottom opening and the bottom opening is adapted to fit a pipette tip rack into which the pipette tips are to be placed; a first row of openings in a first side of the hopper; and a second row of openings in a second side of the hopper, wherein the first row of openings is positioned on the hopper above the second row of openings, and further wherein the first and second row of openings are positioned on adjacent sides of the hopper; (ii) a first alignment comb including a handle and a plurality of teeth extending from the handle, the teeth having a shape that corresponds to openings in the first row of openings in the first side of the hopper; wherein the first alignment comb is slidably positioned through the hopper for orienting pipette tips inside the hopper; and (iii) a second alignment comb including a handle and a plurality of teeth extending from the handle, the teeth having a shape that corresponds to openings in the second row of openings in the second side of the hopper; wherein the second alignment comb is slidably positioned through the hopper for orienting pipette tips inside the hopper; and further wherein the first alignment comb and second alignment comb are inserted through the hopper perpendicular to one another.

A second aspect of the invention is an apparatus including a hopper adapted for receiving one or more pipette tips; a first alignment comb slidably positioned through the hopper for orienting pipette tips inside the hopper; and a second alignment comb slidably positioned through the hopper for orienting pipette tips inside the hopper, wherein the first alignment comb and second alignment comb are inserted through the hopper perpendicular to one another.

A third aspect of the invention is a method for filling a pipette tip rack including (i) inserting a first alignment comb through a first horizontal row of openings in a hopper adapted for receiving a plurality of pipette tips; (ii) pouring a plurality of pipette tips into a top opening in the hopper; (iii) agitating the hopper to begin orienting the pipette tips; (iv) inserting a second alignment comb through a second horizontal row of openings in the hopper; (v) positioning the hopper over a pipette tip rack into which the pipette tips are to be positioned, such that each of the pipette tips is aligned with an opening in the pipette tip rack; and (vi) removing the first alignment comb and the second alignment comb from the hopper.

A feature of the invention is the use of an alignment comb with trough-shaped teeth to orient pipette tips in a hopper.

Another feature of the invention is the use of a second alignment comb that is inserted through the hopper perpendicular to the first alignment comb, and which forces the pipette tips into a grid pattern corresponding to the wells of a pipette tip rack.

Another feature of the invention is that the entire hopper, which contains the pipette tips aligned with the first and second alignment combs, can be positioned over the wells of an empty pipette tip rack and the combs can be removed to allow the tips to drop into the rack wells.

DETAILED DESCRIPTION

Figure 1:
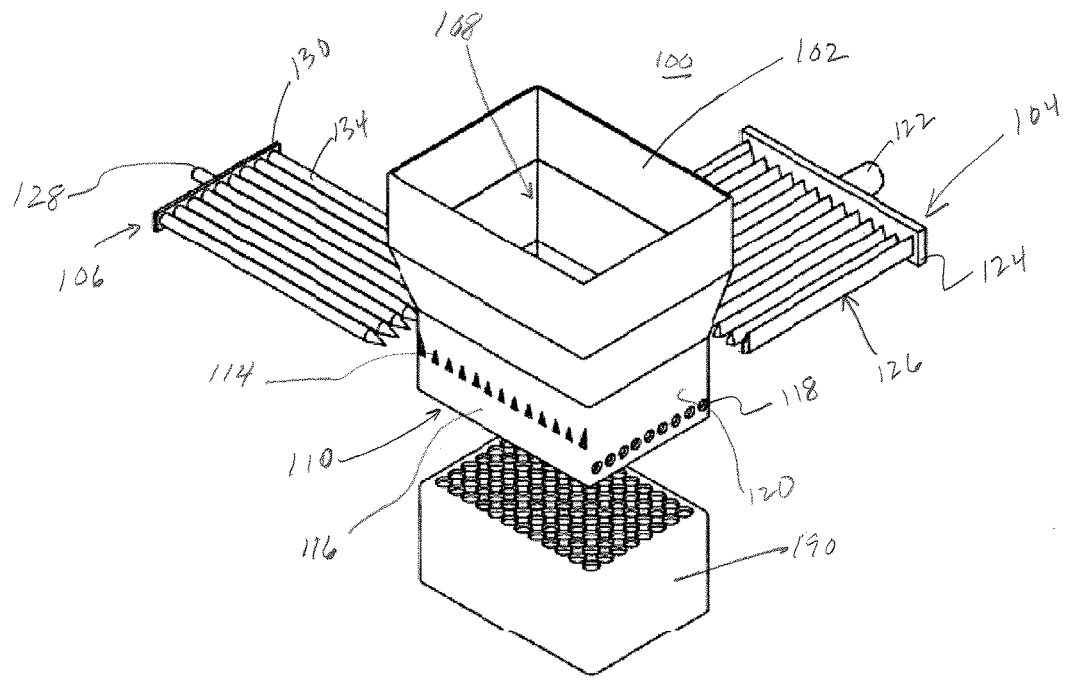
FIG. 1 is a perspective view of an embodiment of a hopper and first and second alignment combs positioned over a pipette tip rack.

Referring generally to FIG. 1, there is shown one of many exemplary embodiments of an apparatus 100 for orienting pipette tips of the present invention. The apparatus 100 comprises a hopper 102, a first alignment comb 104, and a second alignment comb 106. The apparatus 100 can be used on a laboratory bench top to orient and align bulk pipette tips and then to transfer the pipette tips to a single empty well rack 190, e.g., a 96-well rack. For purposes of this invention, the terms "well rack," "pipette rack," and "pipette tip rack"

can be used interchangeably and are intended to mean the same thing, namely, a rack in which pipette tips are stored for later use.

The hopper 102 has a top opening 108 and a bottom opening 110. The top opening 108 optionally but preferably is generally rectangular-shaped and has a perimeter greater than the perimeter of the bottom opening 110, which also optionally but preferably is generally rectangular-shaped. In a preferred embodiment, the bottom opening 110 of the hopper 102 is shaped and sized to correspond to the shape and size of a pipette rack 190 into which the pipette tips are to be transferred through the apparatus 100 of the present invention. In one of many alternative embodiments of the invention, the hopper 100 can include an adapter or other means for adjusting the effective size of the bottom opening 110 of the hopper 102, so the apparatus 100 can be used with well racks 190 of different sizes.

The hopper 102 includes two rows of horizontal openings that correspond to teeth in the first and second alignment combs 104, 106. A first horizontal row of openings 114 extends across a first side 116 of the hopper 102 and is adapted to receive teeth from the first alignment comb 104. The openings 114 optionally but preferably are triangular in shape, and the first horizontal row of openings 114 is higher on the hopper 102 than a second horizontal row of openings 118. The second horizontal row of openings 118 extends across a second side 120 of the hopper 102 and is adapted to receive teeth from the second alignment comb 106. The openings 118 optionally but preferably are circular in shape, and the second row of openings 118 is lower on the hopper 102 than the first horizontal row of openings 114. The first side 116 of the hopper 102 and second side 120 of the hopper 102 optionally but preferably are adjacent to one another, such that the second alignment comb 106 is positioned perpendicular to the first alignment comb 104.

The first alignment comb 104 optionally but preferably has a handle 122, a retention member 124, and a plurality of elongated trough-shaped teeth 126 extending from the retention member 124. Each of the plurality of elongated trough-shaped teeth 126 optionally but preferably has a triangular cross-section shape that corresponds to an opening 114 in the hopper 102. The number of teeth 126, as well as their width and the space between them, in the first alignment comb 104 can be adjusted depending on the size and number of pipette tip openings in the pipette tip rack.

Similarly, the second alignment comb 106 optionally but preferably has a handle 128, a retention member 130, and a plurality of elongated trough-shaped teeth 134 extending from the retention member 130. Each of the plurality of elongated trough-shaped teeth 134 optionally but preferably has a circular cross-section shape that corresponds to an opening 118 in the hopper 102. The number of teeth 134, as well as their width and the space between them, in the second alignment comb 106 can be adjusted depending on the size and number of pipette tip openings in the pipette tip rack.

Figure 2:
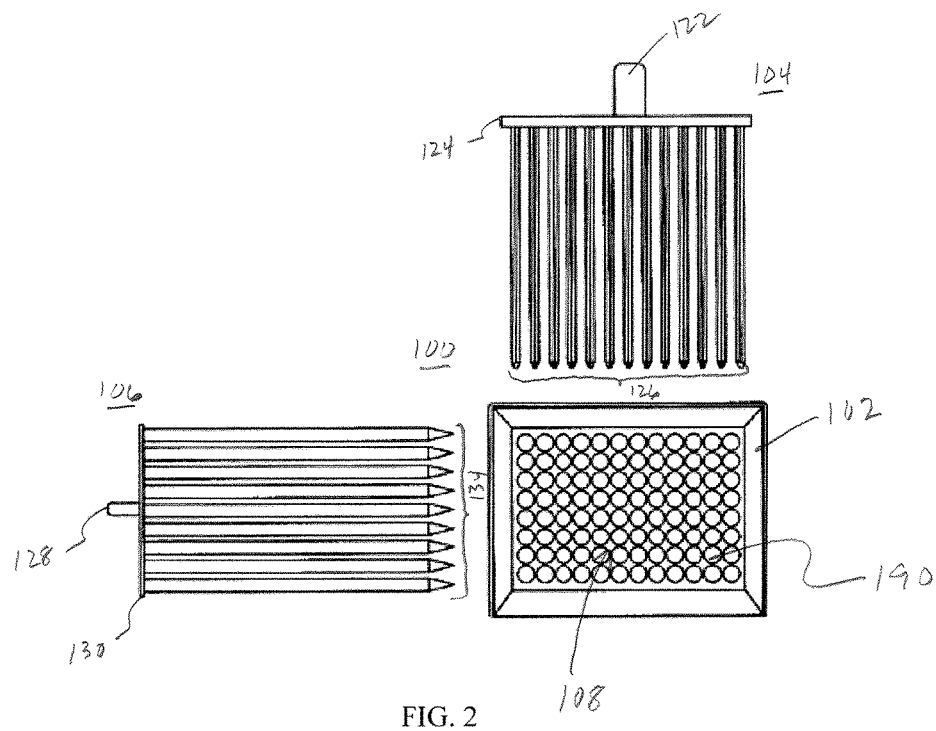
FIG. 2 is a top view of an embodiment of first and second alignment combs positioned relative to a hopper and a pipette tip rack.

As shown in FIG. 2, the hopper 102 can be positioned with its opening 108 above a pipette tip rack 190 into which oriented pipette tips can be inserted. The first alignment comb 104 having a handle 122, a retention member 124, and a plurality of elongated trough-shaped teeth 126 can be inserted through a first horizontal row of openings 114 (see FIG. 1) in the hopper 102. A second alignment comb 106 having a handle 128, retention member 130, and a plurality of elongated trough-shaped teeth 134 can be inserted through a second horizontal row of openings 118 (see FIG. 1). The first alignment comb 104 and second alignment comb 106 are positioned perpendicular to one another.

Figure 3:
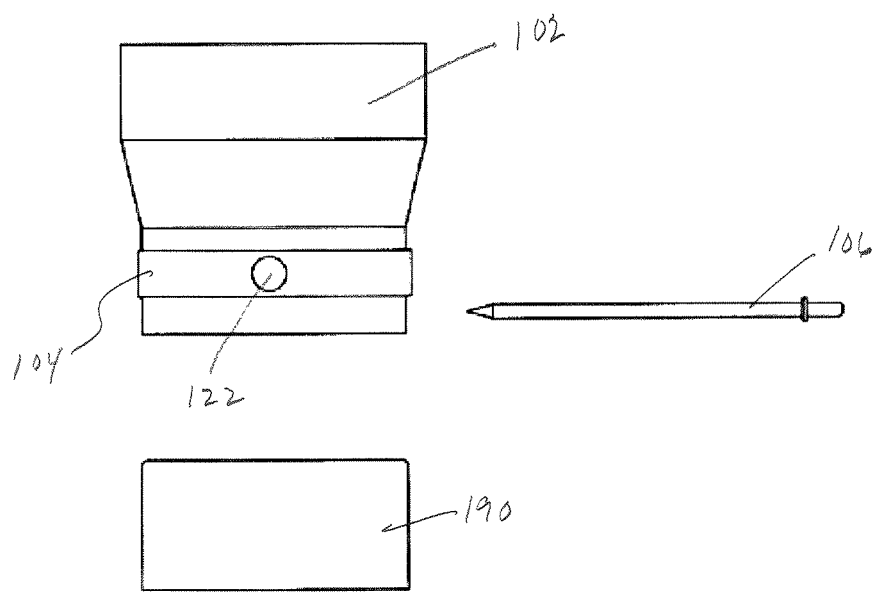
FIG. 3 is a front view of an embodiment of a hopper and an alignment comb positioned over a pipette tip rack.

As shown in FIG. 3, the first alignment comb 104 is inserted through the hopper 102 above the second alignment comb 106, and the second alignment comb 106 is inserted perpendicular to the first alignment comb 104.

In operation, a first alignment comb 104 having a handle 122, a retention member 124, and a plurality of elongated trough-shaped teeth 126 extending from the retention member 124 is inserted through a first horizontal row of openings 114 in a hopper 102. Each of the plurality of elongated trough-shaped teeth 126 optionally but preferably has a triangular cross-section shape that corresponds to an opening 114 in the hopper 102. The number of teeth 126, as well as their width and the space between them, in the first alignment comb 104 can be adjusted depending on the size and number of pipette tip openings in the pipette tip rack. The hopper 102 has a top opening 108 and a bottom opening 110. The top opening 108 optionally but preferably is generally rectangular-shaped and has a perimeter greater than the perimeter of the bottom opening 110, which also optionally but preferably is generally rectangular-shaped. The bottom opening 110 of the hopper 102 is shaped and sized to correspond to the shape and size of a pipette rack 190 into which the pipette tips are to be transferred through the apparatus 100 of the present invention.

A plurality of pipette tips is poured through the top opening 108 into the hopper 102 from a bag of bulk pipette tips. The orientation of the pipette tips is random when the pipette tips are first poured into the hopper 102. The hopper 102 is gently agitated by hand to begin orienting the tips. The apparatus 100 also can include an alternative automatic agitating member to begin orienting the pipette tips. A second alignment comb 106 having a handle 128, a retention member 130, and a plurality of elongated trough-shaped teeth 134 extending from the retention member 130, is inserted through a second horizontal row of openings 118 in the hopper 102 perpendicular to the first alignment comb 104. Each of the plurality of elongated trough-shaped teeth 134 optionally but preferably has a circular cross-section shape that corresponds to an opening 118 in the hopper 102. The number of teeth 134, as well as their width and the space between them, in the second alignment comb 106 can be adjusted depending on the size and number of pipette tip openings in the pipette tip rack. The second alignment comb 106 forces the pipette tips into the same configuration as the wells of the empty pipette tip rack 190. The bottom opening 110 of the hopper 102 is positioned above a pipette tip rack 190, and the aligned pipette tips are lowered over the wells of the empty rack 180. The two alignment combs 104, 106 are removed sequentially to release the pipette tips into the pipette tip rack 190.

CONCLUSION

While various embodiments of the present invention have been described above, it should be understood that they have been presented by way of example only, and not limitation. It will be understood by those skilled in the art that various changes in form and details may be made therein without departing from the spirit and scope of the invention. Thus, the breadth and scope of the invention should not be limited by any of the above-described exemplary embodiments.

What is claimed is:

1. An apparatus, comprising:
   a hopper adapted for receiving one or more pipette tips, the hopper comprising:

a top opening and a bottom opening, wherein the top opening is larger than the bottom opening and the bottom opening is adapted to fit a pipette tip rack into which the pipette tips are to be placed;

a first row of openings in a first side of the hopper; and a second row of openings in a second side of the hopper, wherein the first row of openings is positioned on the hopper above the second row of openings, and further wherein the first and second rows of openings are positioned on adjacent sides of the hopper;

a first alignment comb comprising a handle and a plurality of teeth extending from the handle, the teeth having a shape that corresponds to openings in the first row of openings in the first side of the hopper; wherein the first alignment comb is slidably positioned through the hopper for orienting pipette tips inside the hopper; and a second alignment comb comprising a handle and a plurality of teeth extending from the handle, the teeth having a shape that corresponds to openings in the second row of openings in the second side of the hopper; wherein the second alignment comb is slidably positioned through the hopper for orienting pipette tips inside the hopper; and further wherein the first alignment comb and second alignment comb are inserted through the hopper perpendicular to one another.

2. The apparatus of claim 1, wherein the teeth in the first alignment comb have a triangular shape.

3. The apparatus of claim 1, wherein the teeth in the second alignment comb have a cylindrical shape that terminates in a point.

4. An apparatus, comprising:
a hopper adapted for receiving one or more pipette tips;
a first alignment comb slidably positioned through the hopper for orienting pipette tips inside the hopper; and
a second alignment comb slidably positioned through the hopper for orienting pipette tips inside the hopper, wherein the first alignment comb and second alignment comb are inserted through the hopper perpendicular to one another.

5. The apparatus of claim 4, further comprising an agitating member connected to the hopper for shaking the hopper to begin orienting the pipette tips in the hopper.

6. The apparatus of claim 4, wherein the hopper comprises a top opening and a bottom opening, and further wherein the top opening is larger than the bottom opening and the bottom opening is adapted to fit a pipette tip rack into which the pipette tips are to be placed.

7. The apparatus of claim 4, wherein the hopper further comprises a first row of openings in a first side of the hopper, and a second row of openings in a second side of the hopper; wherein the first row of openings is positioned on the hopper above the second row of openings, and further wherein the first and second row of openings are positioned on adjacent sides of the hopper.

8. The apparatus of claim 7, wherein the first alignment comb comprises a handle and a plurality of teeth extending from the handle.

9. The apparatus of claim 8, wherein the teeth have a shape that corresponds to openings in the first row of openings in the first side of the hopper.

10. The apparatus of claim 9, wherein the teeth have a triangular shape.

11. The apparatus of claim 7, wherein the second alignment comb comprises a handle and a plurality of teeth extending from the handle.

12. The apparatus of claim 11, wherein the teeth have a shape that corresponds to the openings in the second row of openings in the second side of the hopper.

13. The apparatus of claim 12, wherein the teeth have a cylindrical shape that terminates in a point.

14. A method for filling a pipette tip rack, comprising:
inserting a first alignment comb through a first horizontal row of openings in a hopper adapted for receiving a plurality of pipette tips;
pouring a plurality of pipette tips into a top opening in the hopper;
agitating the hopper to begin orienting the pipette tips;
inserting a second alignment comb through a second horizontal row of openings in the hopper;
positioning the hopper over a pipette tip rack into which the pipette tips are to be positioned, such that each of the pipette tips is aligned with an opening in the pipette tip rack; and
removing the first alignment comb and the second alignment comb from the hopper.

15. The method of claim 14, wherein the hopper comprises a top opening and a bottom opening, wherein the top opening is larger than the bottom opening and the bottom opening is adapted to fit a pipette tip rack into which the pipette tips are to be placed.

16. The method of claim 14, wherein the first row of openings is positioned on the hopper above the second row of openings.

17. The method of claim 14, wherein the first and second row of openings are positioned on adjacent sides of the hopper.

18. The method of claim 14, wherein the first alignment comb comprises a handle and a plurality of teeth extending from the handle, the teeth having a shape that corresponds to openings in the first horizontal row of openings in the first side of the hopper; wherein the first alignment comb is slidably positioned through the hopper for orienting pipette tips inside the hopper.

19. The method of claim 14, wherein the second alignment comb comprises a handle and a plurality of teeth extending from the handle, the teeth having a shape that corresponds to openings in the second horizontal row of openings in the second side of the hopper; wherein the second alignment comb is slidably positioned through the hopper for orienting pipette tips inside the hopper; and further wherein the first alignment comb and second alignment comb are inserted through the hopper perpendicular to one another.

* * * * *